(12) United States Patent
Nowak et al.

(10) Patent No.: US 10,029,086 B2
(45) Date of Patent: Jul. 24, 2018

(54) METHOD AND SYSTEM FOR AN ADAPTIVE COUPLING DEVICE FOR MEDICAL CONDUITS

(71) Applicant: The Board of Regents of the University of Texas System, Austin, TX (US)

(72) Inventors: Brent M. Nowak, San Antonio, TX (US); Jayson David Aydelotte, San Antonio, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 658 days.

(21) Appl. No.: 14/388,473

(22) PCT Filed: Mar. 26, 2013

(86) PCT No.: PCT/US2013/033843
§ 371 (c)(1),
(2) Date: Sep. 26, 2014

(87) PCT Pub. No.: WO2013/148655
PCT Pub. Date: Oct. 3, 2013

(65) Prior Publication Data
US 2015/0151103 A1    Jun. 4, 2015

Related U.S. Application Data

(60) Provisional application No. 61/615,643, filed on Mar. 26, 2012.

(51) Int. Cl.
*A61M 39/10*    (2006.01)
*A61M 39/02*    (2006.01)
*A61M 39/26*    (2006.01)
*A61M 39/24*    (2006.01)

(52) U.S. Cl.
CPC .... *A61M 39/1011* (2013.01); *A61M 39/0247* (2013.01); *A61M 39/26* (2013.01);
(Continued)

(58) Field of Classification Search
CPC .......... A61M 39/1011; A61M 39/0247; A61M 39/26; A61M 2039/1027; A61M 2039/248; A61M 2039/263
(Continued)

(56) References Cited

U.S. PATENT DOCUMENTS 4,648,868 A * 3/1987 Hardwick ............ A61B 5/0215
137/625.17
5,207,641 A * 5/1993 Allton ................ A61M 16/0463
137/625.22
(Continued)

FOREIGN PATENT DOCUMENTS

WO    2008/054699    5/2008

OTHER PUBLICATIONS

Watson et al. "Break-aWay Percutaneous Endoscopic Gastrostomy (BW-PEG) Tube" Patent Foundation, University of Virginia (Jul. 2011).
(Continued)

*Primary Examiner* — Manuel Mendez
(74) *Attorney, Agent, or Firm* — Meyertons, Hood, Kivlin, Kowert & Goetzel, P.C.; Mark R. DeLuca

(57) ABSTRACT

This disclosure describes systems and methods for adaptively coupling conduits such as medical tubing to a transcutaneous fixating device or other medical tubing. In some embodiments, an adaptive coupling system for coupling two medical conduits may include a body. The body may include a first opening. The first opening is positioned proximally to a subject. The body may include a second opening. The second opening is positioned distally to the subject. The
(Continued)

body may include a fluid gate. In some embodiments, the fluid gate may be configured to control a flow of fluids through the body between the first opening and the second opening. The first opening may be configured to release a first medical conduit, during use, under a first set of loading conditions. In some embodiments, the second opening may be configured to release a second medical conduit, during use, under a second set of loading conditions.

21 Claims, 3 Drawing Sheets

(52) U.S. Cl.
CPC ............... *A61M 2039/1027* (2013.01); *A61M 2039/248* (2013.01); *A61M 2039/263* (2013.01)

(58) Field of Classification Search
USPC .......................... 137/625.22, 625.17; 604/32
See application file for complete search history.

(56) References Cited

U.S. PATENT DOCUMENTS

| | | |
|---|---|---|
| 5,820,614 A | 10/1998 | Erskine et al. |
| 6,344,033 B1 | 2/2002 | Jepson et al. |
| 2005/0015075 A1 | 1/2005 | Wright et al. |
| 2005/0253389 A1 | 11/2005 | Schulte |
| 2008/0197626 A1 | 8/2008 | Coambs et al. |
| 2010/0286596 A1 | 11/2010 | Hofmann et al. |
| 2011/0011474 A1 | 1/2011 | Duncan |
| 2011/0112482 A1 | 5/2011 | Redd |
| 2011/0266477 A1 | 11/2011 | Stroup |

OTHER PUBLICATIONS

International Search Report/Written Opinion for PCT Application No. PCT/US2013/033843 dated Jul. 17, 2013.
International Preliminary Report on Patentability for PCT Application No. PCT/US2013/033843 dated Oct. 1, 2014.

* cited by examiner

METHOD AND SYSTEM FOR AN ADAPTIVE COUPLING DEVICE FOR MEDICAL CONDUITS

BACKGROUND OF THE INVENTION

1. Field of the Invention

The present disclosure generally relates coupling devices for medical conduits. More particularly, the disclosure generally relates to systems for adaptive coupling devices configured to break under predesigned forces during use as well as inhibiting leaks upon breaking.

2. Description of the Relevant Art

Currently there are many different types of medical access devices used in the medical profession. Medical access devices may include intravenous catheters and feeding tubes. Feeding tubes may be used for total parental nutrition (TPN). Theses and other medical access devices have been historically used in the treatment of hospitalized patients. However, more and more medical access devices are being utilized not just for hospitalized patients but also for people receiving outpatient care. Due to medical access devices being used more and more with patients who have limited and in some cases unlimited mobility there are increasing problems associated with the use of medical access devices. Problems may occur when active patients catch a fluid line attached to the medical access device on an object or in other cases wherein confused patients damaging the fluid line or access device.

Medical tubing commonly consists of polyvinylchloride (PVC) tubing to connect fluid reservoirs and infusion pumps to medical access devices. PVC tubing commonly has a break-force of about ten kilograms or greater. A force of about three kilograms may remove the tape from the skin when tape is used for securing a catheter. In some instances, catheters are secured to the skin with sutures. Any force applied to the sutures would cause significant discomfort to the patient. When an accidental force is applied to the PVC tubing, the tubing generally does not break, instead it often transfers the force to the medical access device. The force possibly pulls the device off or out of the patient, or breaks it off, leading to further complications. The soft silicone rubber tubing, in sizes commonly used in catheters for long term implantation, has a break force of less than about one kilogram.

United States Patent Publication No. 20110112482 issued to Redd (hereinafter "Redd") discloses a break-way PEG tube uses a releasable connector between two tubing segments to facilitate release of a feeding portion of the PEG tube when pulled on to avoid accidental removal of a distal portion of the PEG tube from a patient's abdomen. However, Erskine does not disclose a medical access device which release preferentially under complex loading conditions.

United States Patent Publication No. 20080197626 issued to Coambs et al. (hereinafter "Coambs") discloses a coupling device for coupling a patient-side medical line to an equipment-side medical line. The device includes two parts, one fluidly coupled to each medical line. One of the parts provides both a detachable coupling that detaches when subjected to a sufficient separation force and a secure locking mechanism that requires manual separation. However, Coambs does not disclose a medical access device which release preferentially under complex loading conditions.

U.S. Pat. No. 6,344,033 issued to Jepson et al. (hereinafter "Jepson") discloses a needless connector is provided which utilizes a resealable preslit septum valve. The valve is resiliently restrained relative to a housing with the valve and housing configured to accept a standard male luer lock having a luer tip which penetrates the valve through the opening to extend within the housing and a luer locking flange of the luer lock extending about the housing. However, Jepson does not disclose a medical access device which release preferentially under complex loading conditions.

PCT Patent Publication No. WO 2008/054699 issued to Sage et al. (hereinafter "Sage") discloses a breakaway connector for use with a medical (e.g., catheter) or other fluid system. The connector may include two couplers that engage one another via a substantially frictionless retention device. However, Sage does not disclose a medical access device which release preferentially under complex loading conditions.

U.S. Pat. No. 5,820,614 issued to Erskine et al. (hereinafter "Erskine") discloses a disconnect device for placement in a medical tubing set. However, Erskine does not disclose a medical access device which release preferentially under complex loading conditions. Although there exist many different types of medical access devices, none of the known devices accomplish what the herein described medical access device is capable of.

What is needed is a device which allows one to safely and predictably couple and uncouple a medical access device from a subject. The device which therefore inhibits premature uncoupling and leaking prior to and after uncoupling.

SUMMARY

This disclosure describes systems and methods for adaptively coupling conduits such as medical tubing to a transcutaneous fixating device or other medical tubing. In some embodiments, an adaptive coupling system for coupling two medical conduits may include a body. The body may include a first opening. The first opening is positioned proximally to a subject. The body may include a second opening. The second opening is positioned distally to the subject. The body may include a fluid gate. In some embodiments, the fluid gate may be configured to control a flow of fluids through the body between the first opening and the second opening. The first opening may be configured to release a first medical conduit, during use, under a first set of loading conditions. In some embodiments, the second opening may be configured to release a second medical conduit, during use, under a second set of loading conditions.

In some embodiments, the first set of loading conditions may be different from the second set of loading conditions. The first set of loading conditions may include tension. The first set of loading conditions may include torsion. The first set of loading conditions may include bending. The first set of loading conditions may include shear loads. The first set of loading conditions may include a combination of at least two of tension, torsion, bending, and shear load.

In some embodiments, the fluid gate is configured to allow unidirectional flow. The fluid gate may function to allow bidirectional flow. The fluid gate may function to inhibit fluids exiting the first opening when the first opening releases, during use, a first medical conduit. The fluid gate may function to inhibit fluids exiting the second opening when the second opening releases, during use, a second medical conduit. The fluid gate may function to be biased towards a closed which inhibits fluids from moving through the body. In some embodiments, at least one bias member is configured to apply pressure to a gate such that when one of the first or second openings is uncoupled the gate inhibits fluids from passing through the body. The fluid gate may include a substantially spherical gate. The fluid gate may include a substantially hemispherical gate.

In some embodiments, the fluid gate may include a first fluid gate. The first fluid gate may function to control a flow of fluids through the body moving in a first direction from the first opening to the second opening. The fluid gate may include a second fluid gate configured to control a flow of fluids through the body moving in a second direction from the second opening to the first opening.

BRIEF DESCRIPTION OF THE DRAWINGS

Advantages of the present invention may become apparent to those skilled in the art with the benefit of the following detailed description of the preferred embodiments and upon reference to the accompanying drawings.

Figure 1A:
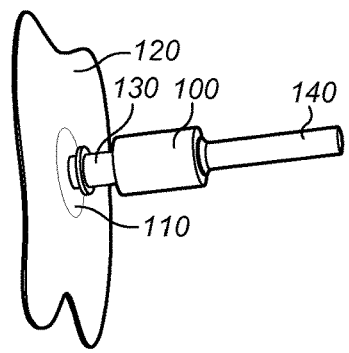
FIG. 1A depicts a diagram of a perspective view of an embodiment of an adaptive coupler coupling a subject and medical tubing.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

Definitions

Unless defined otherwise, all technical and scientific terms used herein have the same meaning as commonly understood by one of ordinary skill in the art.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

The term "proximal" as used herein generally refers to a region nearest to a subject or a patient (e.g., proximity to the transcutaneous insertion point).

The term "distal" as used herein generally refers to a region furthest to a subject or a patient (e.g., proximity to the transcutaneous insertion point).

FIG. 1A depicts a diagram of a perspective view of an embodiment of adaptive coupling system 100 coupling a subject and medical tubing. In some embodiments, adaptive coupling system 100 may connect conduits (e.g., medical tubing). The adaptive coupling system may connect conduits in a serial fashion. The adaptive coupling system may connect, for example, to gastric tube 130 at a first end (herein the proximal end). The adaptive coupling system may connect, for example, to feed or drain tube 140 on the other second end (herein the distal end). The proximal and distal adjectives provide descriptors of the coupler attachment ends, which are defined through their proximity to transcutaneous insertion point 110.

In some embodiments, gastric tube 130 is attached to transcutaneous fixating device 110. The fixating device may provide a seal between body wall 120 and atmosphere. The fixating device may provide a means to attach the gastric tube. The fixating device may provide an example of a secure attachment site to which an adaptive coupling system may be attached. In some embodiments, while certain transcutaneous sites may be compliant, the adaptive coupling system will release under almost all loading conditions prior to the release of the transcutaneous fixating device.

In some embodiments, adaptive coupling system 100 is a substantially universal system. The component arrangement in the figure(s) or description(s) herein does not imply a fluid flow direction. The "drain tube" does not define or limit its functionality; the term "drain tube" does not restrict the utility of this tube, which could be used as a feed tube, drain tube, or the like. In a similar fashion the "gastric tube" may fulfill multiple utilities.

If acting as a body drain, or the like, the fluid may originate within the body, then flow through the transcutaneous fixating device, gastric tube, adaptive coupler, and out through the drain tube. If acting as a feed tube, or the like, the fluid may originate upstream of the feed tube, then flow through the adaptive coupler, gastric tube, and the transcutaneous fixating device. Beyond, yet including medical applications, the adaptive coupling system may attach to any functional tube that passes a wide range of matter, such as but not limited to, Newtonian or non-Newtonian fluids, compressible gasses, fluids (compressible and incompressible) with particulates or other matter, or the like.

In some embodiments, an adaptive coupling system may be configured to couple to all existing tubing couplers (e.g. any type of barbed end device). In some embodiments, an adaptive coupling system may inhibit fluids from flowing out of undesirable openings etc. (e.g., leaks). Undesirable leaks may be inhibited during installed and normal operating conditions during use (e.g., when the adaptive coupling system is attached to medical tubing, etc.). Undesirable leaks may be inhibited after a predesigned release (i.e. seals and prevents leaks).

In some embodiments, an adaptive coupling system may provide bi-directional flow. In some embodiments, an adaptive coupling system may provide unidirectional flow.

In some embodiments, an adaptive coupling system may release preferentially under complex loading conditions. In some embodiments, complex loading conditions may include tension (e.g. pulling). In some embodiments, complex loading conditions may include torsion (e.g. twisting). In some embodiments, complex loading conditions may include bending. In some embodiments, complex loading conditions may include shear loads (e.g. pinching). In some embodiments, complex loading conditions may include a designed combination of tension, torsion, shear, and/or bending.

In some embodiments, an adaptive coupling system may different release conditions at a proximal end and a distal end of the adaptive coupling system. For example, a proximal end releases under a tension plus torsion loading only, while a distal end release under bending only, or any combination thereof.

In some embodiments, an adaptive coupling system may distinguish between the rate of loading applied including, but not limited to, constant or continuous loading. In some embodiments, an adaptive coupling system may distinguish between the rate of loading applied including dynamic kinematics. Dynamic kinematics may include high velocity or pulse loading. Dynamic kinematics may include sharp accelerations or jerk (i.e., $3^{rd}$ derivative kinematics).

In some embodiments, an adaptive coupling system may provide for visible cues of partial loading conditions by external color change of the device (e.g. change from blue to bright orange at high strain location). Different dyes and/or microencapsulated dyes may be used to achieve such an effect. This may function as a visual indicator that allows professionals (e.g., doctors, nurses, etc.) to quickly assess whether or not an adaptive coupling system has been exposed to unnecessary stresses. Stresses may cause failure which is not immediately visually apparent without such visible cues.

In some embodiments, an adaptive coupling system may be recyclable.

In some embodiments, an adaptive coupling system may be disposable.

Figure 1B:
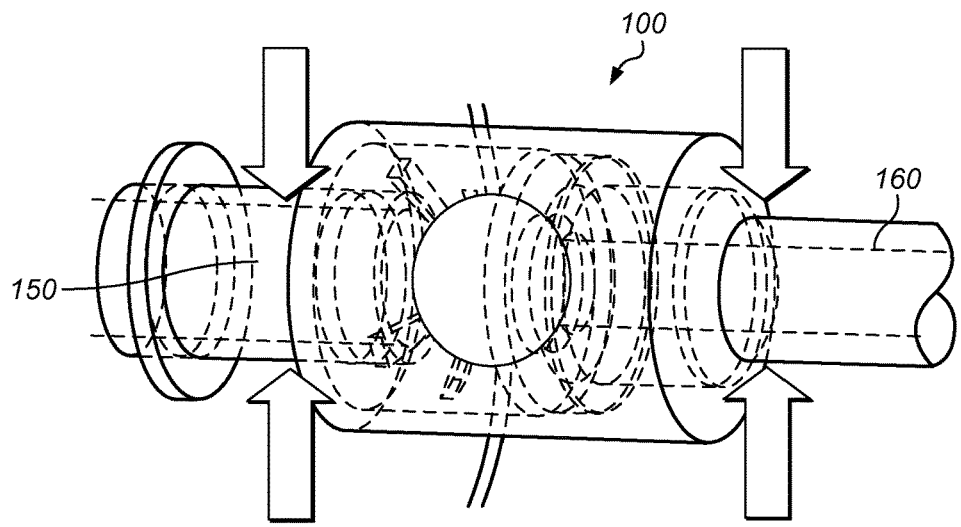
FIG. 1B depicts a diagram of a perspective view of an embodiment of an adaptive coupler coupling to medical tubing at the blue arrows.

FIG. 1B depicts a diagram of a perspective view of an embodiment of adaptive coupler 100 coupling to conduit 150 and conduit 160 and medical tubing at the arrows. As shown in FIG. 1B, (via arrows), the proximal and distal ends of the adaptive coupling system provide a force-fit seal between the conduits outer-diameter and the adaptive coupler's inner diameter. In some embodiments, the force-fit seal may be assisted through the use of barbed inserts (not shown). In some embodiments, the sealing may be assisted by the use of O-rings (not shown), a labyrinth seal, and/or sealed snap rings.

Figure 2:
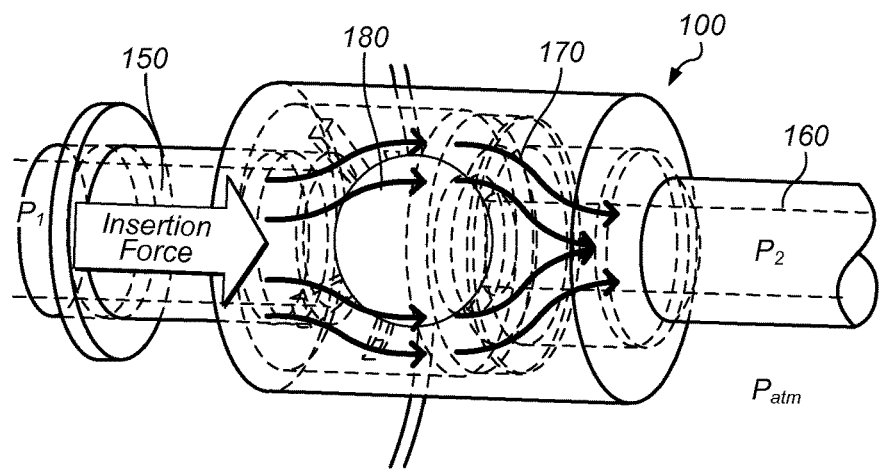
FIG. 2 depicts a diagram of a perspective view of an embodiment of an adaptive coupler wherein an insertion force of a gastric tube allows fluids to flow around a sphere.

FIG. 2 depicts a diagram of a perspective view of an embodiment of adaptive coupler 100 wherein an insertion force of conduit 150 allows fluids 170 to flow around a sphere. The embodiment of gate 180 for controlling the flow of fluids is depicted as a sphere in FIG. 2; however, the gate may have other shapes. Although it should be pointed out that a using a gate with a substantially spherical shape may have advantages. A spherical shaped gate does not have to be oriented in a specific direction as an irregularly shaped gate might have to be. For illustration only, a pressure $P_1$ (depicted in FIG. 2) is greater than the downstream pressure $P_2$, which is greater than atmospheric pressure, $P_{atm}$. As shown below, FIG. 2, when conduit 150 (or a barbed end conduit commonly used in the medical field, not shown in FIG. 2) is inserted into the adaptive coupling system, the gate (e.g., sphere) is shifted to the right creating a gap around the sphere. The gap allows fluid 170 (shown as the plurality of smaller arrows) to flow around the sphere.

Figure 3:
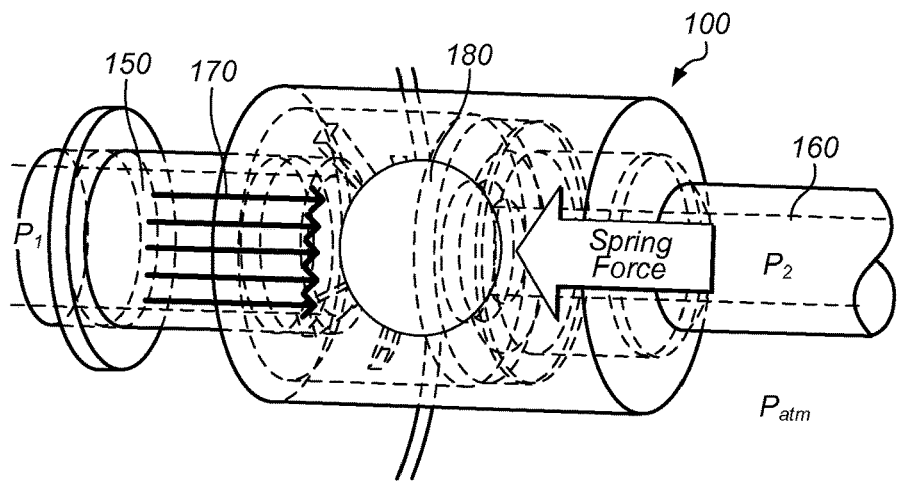
FIG. 3 depicts a diagram of a perspective view of an embodiment of an adaptive coupler wherein when an insertion force of a gastric tube is removed a sphere is moved to inhibit fluids from flowing through the adaptive coupler.

FIG. 3 depicts a diagram of a perspective view of an embodiment of adaptive coupler 100 wherein when an insertion force of conduit 150 is removed gate 180 may be moved to inhibit fluids 170 from flowing through the adaptive coupler. As depicted in FIG. 3, when conduit 150 is decoupled or otherwise preferentially released, the spring force within the adaptive coupler overcomes the internal pressure of the system, thereby, overcoming the delta-pressure preventing any further flow.

As depicted in FIGS. 2 and 3 the ball release and seal mechanism may be duplicated for the distal end of the adaptive coupling system. The actions may be mirror images of the embodiments depicted in FIGS. 2 and 3. Consequently, sealing functionality may be bi-directional.

Figure 4:
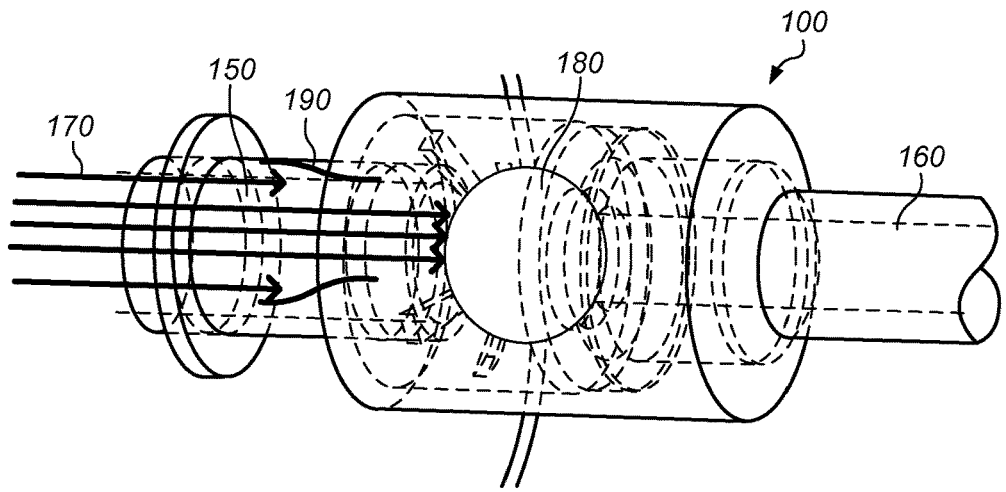
FIG. 4 depicts a diagram of a perspective view of an embodiment of an adaptive coupler wherein an insertion force of a gastric tube allows fluids to flow around a sphere and a second closure mechanism using hemispherical flaps.
Figure 5:
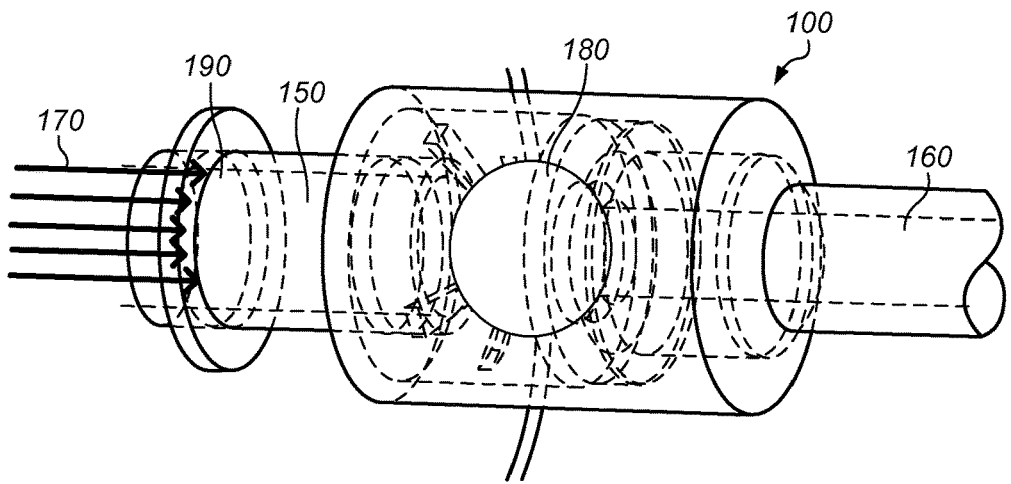
FIG. 5 depicts a diagram of a perspective view of an embodiment of an adaptive coupler wherein when an insertion force of a gastric tube is removed a sphere is moved to inhibit fluids from flowing through the adaptive coupler, as well as a second closure mechanism including hemispherical flaps which revert to a biased closed state.

FIG. 4 depicts a diagram of a perspective view of an embodiment of adaptive coupler 100 wherein an insertion force of conduit 150 allows fluids to flow around a sphere and a second gate 190. The second gate depicted in FIG. 4 may include hemispherical flaps. Hemispherical flaps may be biased such that the flaps are closed when no pressure or insufficient pressure is applied to the flaps. FIG. 5 depicts a diagram of a perspective view of an embodiment of adaptive coupling system 100 wherein when an insertion force of conduit 150 is removed a sphere is moved to inhibit fluids 170 from flowing through the adaptive coupler, as well as a second closure mechanism including hemispherical flaps which revert to a biased closed state. Typically a second gate may include two hemispherical flaps. In some embodiments, more than two hemispherical flaps may be used (e.g., 3, 4, 5, 6, etc.).

Figure 6:
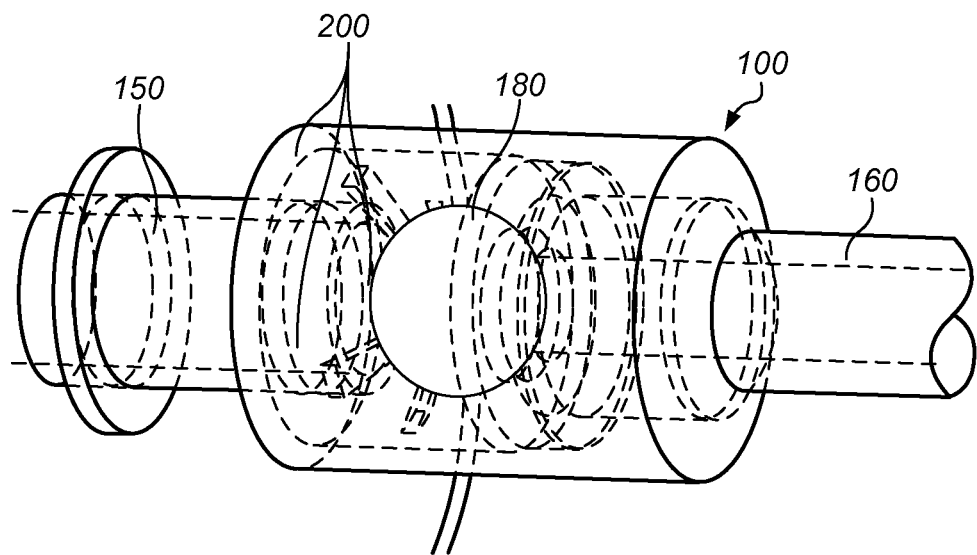
FIG. 6 depicts a diagram of a perspective view of an embodiment of an adaptive coupler wherein spring forces resulting from an internal geometry are shown with arrows.

The sealing forces represented by the arrow in FIG. 3, labeled "spring force", are envisioned to be realized through coils springs, disk springs, conical springs, or inherent in the structure through the molding and/or other manufacturing process. One example of this structure is illustrated in FIG. 6. FIG. 6 depicts a diagram of a perspective view of an embodiment of adaptive coupling system 100 wherein spring forces 200 resulting from an internal geometry are depicted.

In some embodiments, adaptive coupling system 100 may provide bi-directional flow. In some embodiments, adaptive coupling system 100 may provide unidirectional flow. In some embodiments, flow direction may be controlled through a dynamic balancing of the upstream pressure, $P_1$, downstream pressure, $P_2$ with the internal spring forces, $F_S$. Another realization of this functionality may be provided through an embodiment using dual-hemispherical flaps, such that the flow is only unidirectional in all cases.

In some embodiments, an adaptive coupling system may release preferentially under complex loading conditions. In some embodiments, complex loading conditions may include tension (e.g. pulling). In some embodiments, complex loading conditions may include torsion (e.g. twisting). In some embodiments, complex loading conditions may include bending. In some embodiments, complex loading conditions may include shear loads (e.g. pinching). In some embodiments, complex loading conditions may include a designed combination of tension, torsion, shear, and/or bending.

In some embodiments, an adaptive coupling system may different release conditions at a proximal end and a distal end of the adaptive coupling system. For example, a proximal end releases under a tension plus torsion loading only, while a distal end release under bending only, or any combination thereof.

In some embodiments, an adaptive coupling system may distinguish between the rate of loading applied including, but not limited to, constant or continuous loading. In some embodiments, an adaptive coupling system may distinguish between the rate of loading applied including dynamic kinematics. Dynamic kinematics may include high velocity or pulse loading. Dynamic kinematics may include sharp accelerations or jerk (i.e., $3^{rd}$ derivative kinematics).

Preferential release is the response of the adaptive coupling system to pre-defined loading conditions. These may be simplex loads such as tension or pulling only; torsion or twising only; or bending only. Additionally, preferential release is envisioned to be the response to a complex combination of loads.

In some embodiments, the purpose of preferential release by the adaptive coupling system is to allow a release, without loss of fluids, under atypical loading conditions. Atypical loading conditions may be the result of intentional or accidental extraction of intubation by the patient.

In some embodiments, the design of the adaptive coupling system includes, but is not limited to, the use of selective materials (e.g., medical grade polymers, stainless steels, titanium, etc.), which, in some embodiments of the invention, include fibers and or springs that provide structural pre-loading. Under appropriate atypical loading conditions, the pre-loads are overcome, thereby releasing one or both ends of the adaptive coupling system.

In some embodiments, after fabrication, casting, molding, or machining, the material is heat-treated to create directional or bulk material property changes. These directional or bulk material property changes may fail (such that release occurs at a predetermined load or complex load) or preferentially release.

Figure 7:
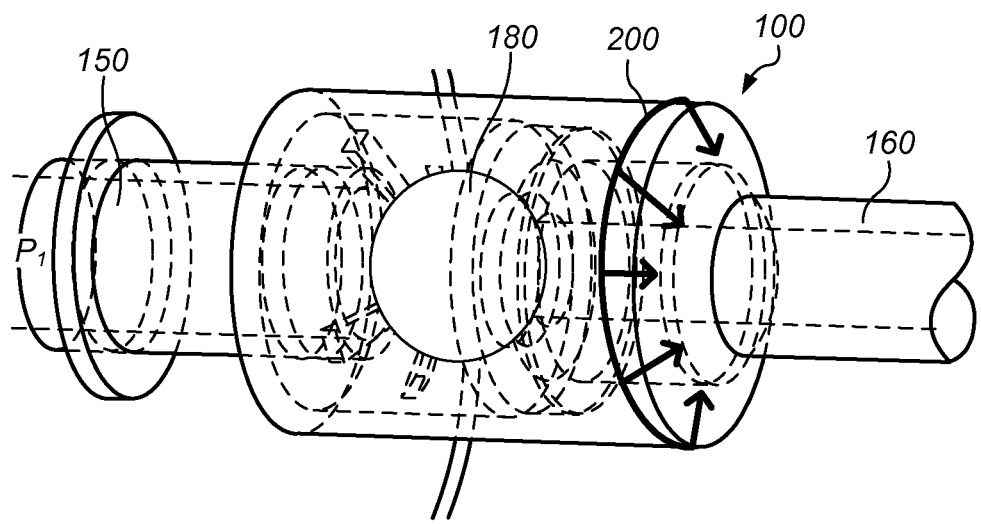
FIG. 7 depicts a diagram of a perspective view of an embodiment of an adaptive coupler including cylindrical cams or over-center mechanisms which release under atypical loading.

In some embodiments, cylindrical cams and over-center mechanisms are incorporated within the adaptive coupling system that release on one or both ends under atypical loading. FIG. 7 depicts a diagram of a perspective view of an embodiment of adaptive coupling system 100 including cylindrical cams 200 or over-center mechanisms which release under atypical loading.

In some embodiments, the adaptive coupling system includes an internal knife-edge. Under atypical loading conditions the knife-edge releases or is pressed against the polymer adaptive coupling system housing, thereby preferentially releasing while not providing a knife-edge that is sufficient to scratch or cut the patient. That is, the knife-edge may completely initiate a preferential release in the form a tear or predetermined failure of the material.

In some embodiments, a brittle material including, but not limited to, ceramic or glass-like polymers are incorporated (e.g., cast, machined, mounted, etc.) within the adaptive coupling system that provides preferential release characteristics.

In some embodiments, an adaptive coupling system may provide visible cues of at least partial loading conditions by external color change of the device (e.g., change from blue to bright orange at a location which has experienced high strains or from excessive loads). Under some conditions significant loading may occur that does not cause preferential release of the adaptive coupling system. This may result in damage to the transcutaneous interface or damage to the adaptive coupling system. The adaptive coupling system may include indicators such that professionals can quickly determine if the system has been subjected to a significant load event. In some embodiments, a color change may be used to reflect these conditions. In some embodiments, color changing strain, pressure, or stress strips may be integrated into the adaptive coupling system. In some embodiments, use of micro-encapsulated pigments which release within the polymer that cause an immediate and highly visible surface color change of the adaptive coupling system may be employed.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An adaptive coupling system for coupling two medical conduits, comprising:
   a body
   a first opening, wherein the first opening is positioned proximally to a subject;
   a second opening, wherein the second opening is positioned distally to the subject; and
   a fluid gate which is configured to control a flow of fluids through the body between the first opening and the second opening;
   a bias member configured to apply pressure to the fluid gate, wherein pressure from the bias member biases the fluid gate against one of the first or second openings to inhibit fluids from moving through the body;
   wherein the first opening is configured to release a first medical conduit, during use, under a first set of loading conditions, and wherein the second opening is configured to release a second medical conduit, during use, under a second set of loading conditions.

2. The system of claim 1, wherein the first set of loading conditions is different from the second set of loading conditions.

3. The system of claim 1, wherein the first set of loading conditions comprises tension.

4. The system of claim 1, wherein the first set of loading conditions comprises torsion.

5. The system of claim 1, wherein the first set of loading conditions comprises bending.

6. The system of claim 1, wherein the first set of loading conditions comprises shear loads.

7. The system of claim 1, wherein the first set of loading conditions comprises a combination of at least two of tension, torsion, bending, and shear load.

8. The system of claim 1, wherein the fluid gate is configured to allow unidirectional flow.

9. The system of claim 1, wherein the fluid gate is configured to allow bidirectional flow.

10. The system of claim 1, wherein the fluid gate is configured to inhibit fluids exiting the first opening when the first opening releases, during use, a first medical conduit.

11. The system of claim 1, wherein the fluid gate is configured to inhibit fluids exiting the second opening when the second opening releases, during use, a second medical conduit.

12. The system of claim 1, wherein at least one bias member is configured to apply pressure to a gate such that when one of the first or second openings is uncoupled the gate inhibits fluids from passing through the body.

13. The system of claim 1, wherein the fluid gate comprises a substantially spherical gate.

14. The system of claim 1, wherein the fluid gate comprises a substantially hemispherical gate.

15. The system of claim 1, wherein the fluid gate comprises a substantially hemispherical flap.

16. The system of claim 1, wherein the fluid gate comprises at least two substantially hemispherical flaps.

17. The system of claim 16, wherein the hemispherical flaps are biased such that fluids are inhibited from being conveyed through the hemispherical flaps.

18. The system of claim 1, wherein the fluid gate comprises:
a first fluid gate configured to control a flow of fluids through the body moving in a first direction from the first opening to the second opening; and
a second fluid gate configured to control a flow of fluids through the body moving in a second direction from the second opening to the first opening.

19. The system of claim 1, wherein the fluid gate is a spherical ball, and wherein pressure from the bias member forces the spherical ball one of the first or second openings to inhibit fluids from moving through into the first or second opening.

20. A method of transferring fluids to a patient comprising:
coupling an adaptive coupling system to two medical conduits, the adaptive coupling system comprising:
a body
a first opening, wherein the first opening is positioned proximally to a subject;
a second opening, wherein the second opening is positioned distally to the subject; and
a fluid gate which is configured to control a flow of fluids through the body between the first opening and the second opening;
a bias member configured to apply pressure to the fluid gate, wherein pressure from the bias member biases the fluid gate against one of the first or second openings to inhibit fluids from moving through the body;
wherein the first opening is configured to release a first medical conduit, during use, under a first set of loading conditions, and wherein the second opening is configured to release a second medical conduit, during use, under a second set of loading conditions; and
wherein one of the first medical conduit or the second medical conduit is coupled to the patient;
transferring fluid to the patient through the adaptive coupling system, wherein if one of the first or second medical conduits are removed, fluid flow through the adaptive coupling system is inhibited.

21. The system of claim 20, wherein the fluid gate is a spherical ball, and wherein pressure from the bias member forces the spherical ball one of the first or second openings to inhibit fluids from moving through into the first or second opening.

* * * * *